(12) United States Patent
Wada et al.

(10) Patent No.: US 6,798,498 B2
(45) Date of Patent: Sep. 28, 2004

(54) APPARATUS FOR EVALUATING POLYSILICON FILM

(75) Inventors: Hiroyuki Wada, Kanagawa (JP); Koichi Tatsuki, Kanagawa (JP); Nobuhiko Umezu, Kanagawa (JP); Eiji Isomura, Kanagawa (JP); Tetsuo Abe, Kanagawa (JP); Tadashi Hattori, Kanagawa (JP); Akifumi Ooshima, Kanagawa (JP); Makoto Uragaki, Kanagawa (JP); Yoshiyuki Noguchi, Kanagawa (JP); Hiroyuki Tamaki, Kanagawa (JP); Masataka Ebe, Kanagawa (JP); Tomohiro Ishiguro, Kanagawa (JP); Yasuyuki Kato, Kanagawa (JP)

(73) Assignees: Sony Corporation, Tokyo (JP); Sony Precision Technology Inc., Tokyo (JP)

( * ) Notice: Subject to any disclaimer, the term of this patent is extended or adjusted under 35 U.S.C. 154(b) by 255 days.

(21) Appl. No.: 10/050,542

(22) Filed: Jan. 18, 2002

(65) Prior Publication Data

US 2002/0145733 A1 Oct. 10, 2002

(30) Foreign Application Priority Data

Jan. 22, 2001 (JP) .......................... 2001-013498
Nov. 27, 2001 (JP) .......................... 2001-360959

(51) Int. Cl.[7] ............................................. G01N 21/00
(52) U.S. Cl. ................................... 356/30; 438/16
(58) Field of Search ....................... 356/445, 446, 356/30; 438/14, 16

(56) References Cited

U.S. PATENT DOCUMENTS

| | | | | |
|---|---|---|---|---|
| 5,314,831 A | * | 5/1994 | Hirae et al. | 356/30 |
| 5,548,661 A | * | 8/1996 | Price et al. | 382/133 |
| 5,825,498 A | * | 10/1998 | Thakur et al. | 356/394 |
| 6,023,056 A | * | 2/2000 | Fiete et al. | 250/201.7 |
| 6,094,223 A | * | 7/2000 | Kobayashi | 348/354 |
| 6,673,639 B2 | * | 1/2004 | Wada et al. | 438/14 |

* cited by examiner

*Primary Examiner*—Richard A. Rosenberger
(74) *Attorney, Agent, or Firm*—Oblon, Spivak, McClelland, Maier & Neustadt, P.C.

(57) ABSTRACT

A polysilicon film evaluation apparatus is provided which enables objective automatic evaluation of the status of a polysilicon film, as formed to a high accuracy in a contact-free fashion. To this end, there is provided a polysilicon film evaluation apparatus 1 including a stage 25 on which to set a substrate W carrying a polysilicon film, an optical system for observation with the visible light 4, 8, 12, 40a for illuminating the visible light on a substrate W on the stage to photograph a surface image of the polysilicon film on the substrate W to effect auto-focusing, an optical system for observation with UV light 6, 10, 40b for illuminating the UV light on the substrate on the stage to acquire a surface image of the polysilicon film of the substrate, auto-focused using the optical system for observation with the visible light, and an evaluating unit 51 for evaluating the linearity and periodicity of a spatial structure of the film surface of the polysilicon film, from a surface image of the polysilicon film obtained by the optical system for observation with UV light, to evaluate the status of the polysilicon film based on the results of evaluation of the linearity and periodicity.

9 Claims, 12 Drawing Sheets

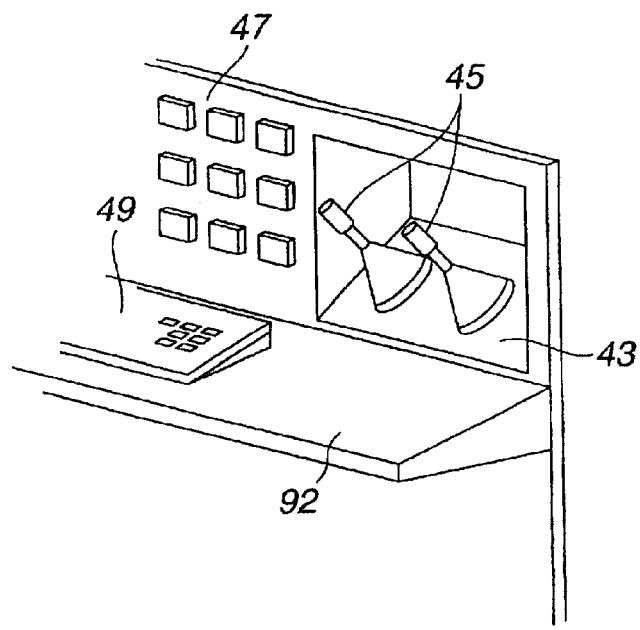
FIG.7
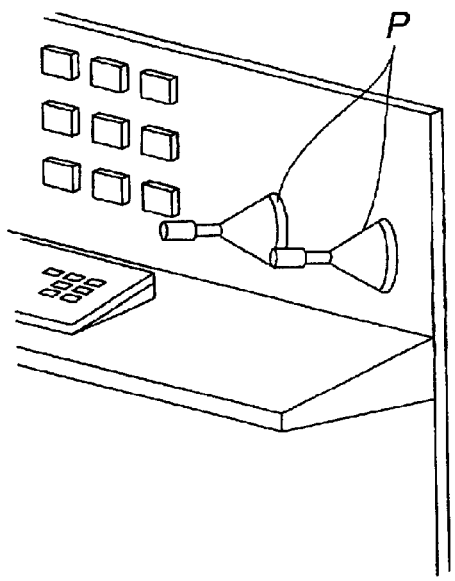 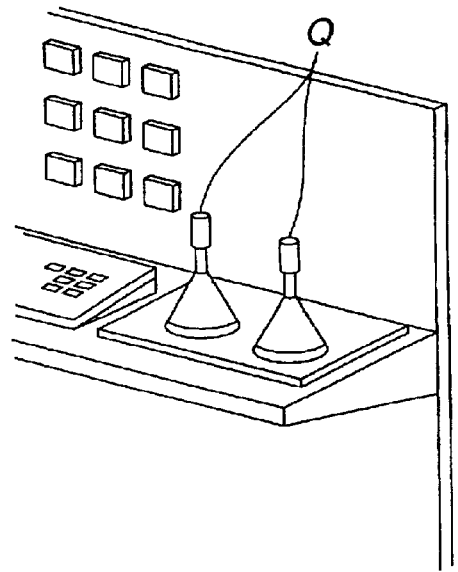
FIG.8A  FIG.8B

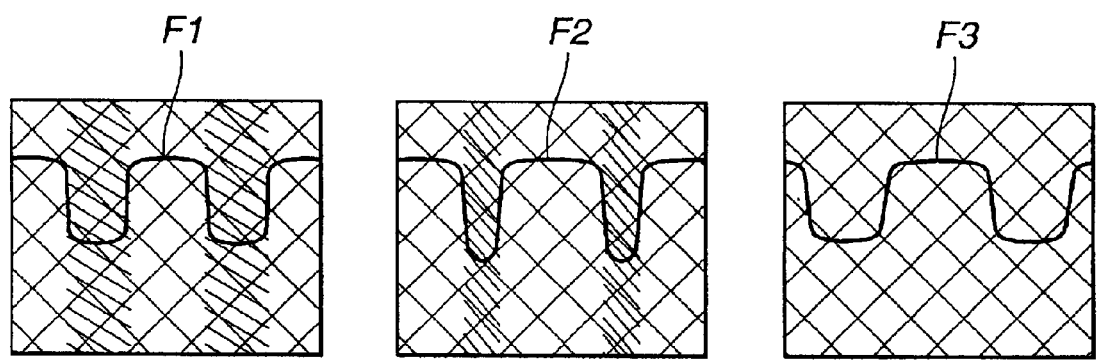
FIG.16A   FIG.16B   FIG.16C
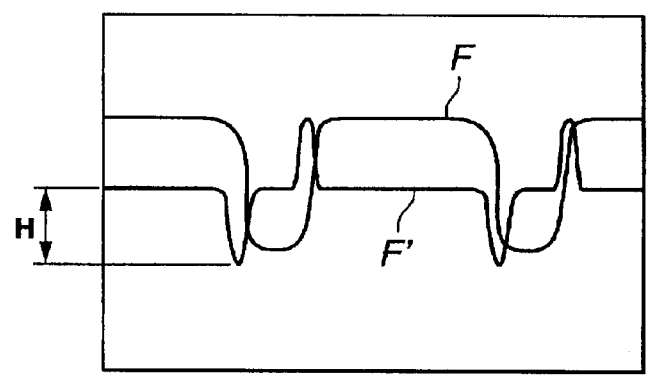
FIG.17

APPARATUS FOR EVALUATING POLYSILICON FILM

BACKGROUND OF THE INVENTION

1. Field of the Invention

This invention relates to an apparatus for evaluating the state of a polysilicon film generated on annealing amorphous silicon.

2. Description of Related Art

Recently, a thin-film transistor, employing a polysilicon film as its channel layer, is being put to practical use. Such the thin-film transistor employing a polysilicon film is appreciably improved in electrical field mobility, so that electric devices e.g., liquid crystal display device, using the thin-film transistor as driving circuit devices, can be improved significantly in definition, operating speed and miniaturization.

On the other hand, development of the so-called low-temperature poly-crystallization process, in which amorphous silicon is heat-treated to form a polysilicon film using a excimer laser annealing device, is also under way. By applying this low-temperature poly-crystallization process as the manufacturing process for the thin-film transistor, thermal damage to the glass substrate may be diminished to permit the use of an inexpensive large-area heat-resistant glass substrate.

However, the excimer laser annealing device, used in the low-temperature poly-crystallization process, is unstable in laser output power, with the result that the grain size of the polysilicon film formed is fluctuated significantly. The result is that the polysilicon film, prepared using this excimer laser annealing device, is not necessarily of the optimum grain size, thus occasionally being discarded as a reject.

So, the conventional practice in carrying out the annealing using this excimer laser annealing device is to perform 100% inspection or sampling inspection, at a stage of completion of the poly-crystallization of the polysilicon film, and to check for the state of crystals of the polysilicon film formed on the uppermost surface of the polysilicon film, thereby to decide whether or not the products are acceptable at this stage. Additionally, the information on the energy afforded from the excimer laser annealing device to the polysilicon film is fed back to the excimer laser annealing device to set an optimum laser power.

However, there has not been a method which objectively evaluates the polysilicon film in non-contact fashion, while there has been a subjective method such as a sensual method of photographing a surface image, using a microscope for visible light or a scanning electron microscope, to visually inspect the surface image to check for the crystal state by a operator. In addition, this known method has other problems that it can not be used as an in-process method, because it is costly and time-consuming. Among other known methods, the spectroscopic evaluation method by ellipsography is not satisfactory as to its quantitative characteristics.

SUMMARY OF THE INVENTION

In view of the above depicted status of the art, it is an object of the present invention to provide a polysilicon film evaluating apparatus whereby the status of the as-formed polysilicon film can be evaluated to a high accuracy objectively automatically in a non-contact fashion.

The present invention provides an apparatus for evaluating a polysilicon film formed on annealing an amorphous silicon film, including a stage for setting a substrate thereon, the substrate carrying a polysilicon film formed thereon, an optical system for observation with the visible light, the optical system for observation with the visible light illuminating the visible light on the substrate on the stage for photographing a surface image of the polysilicon film on the substrate to effect auto-focusing, an optical system for observation with UV light, illuminating the UV light on the substrate on the stage for acquiring a surface image of the polysilicon film on the substrate, auto-focused using the optical system for observation with the visible light, and evaluation means for evaluating the linearity and periodicity of a spatial structure of the film surface of the polysilicon film from the surface image of the polysilicon film acquired by the optical system for observation with UV light to evaluate the state of the polysilicon film based on the results of evaluation of the linearity and periodicity.

With the apparatus for evaluating a polysilicon film, according to the present invention, the status of the as-formed polysilicon film can be evaluated to a high accuracy objectively automatically in a non-contact fashion.

BRIEF DESCRIPTION OF THE DRAWINGS

FIG. 7 is an enlarged perspective view showing the layout of a joystick of the polysilicon film evaluating apparatus shown in FIG. 4.

FIG. 8 is an enlarged perspective view showing a typical layout of a conventional joystick.

FIGS. 16A to 16C show surfaces of polysilicon films with luminosity superposed thereon.

FIG. 17 shows the surfaces of FIGS. 16A to 16C with changes in luminosity superposed thereon.

DESCRIPTION OF THE PREFERRED EMBODIMENTS

Figure 1A:
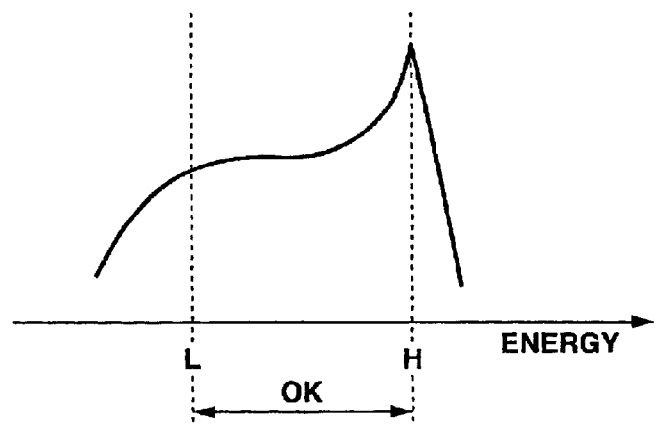
FIG. 1A illustrates the relationship between the grain size of a polysilicon film and the energy afforded through excimer laser annealing.

Referring to the drawings, preferred embodiments of the present invention will be explained in detail.

A polysilicon film evaluating apparatus, embodying the present invention, is used for inspecting a polysilicon film formed during the production process of e.g., a thin film transistor having a bottom gate structure (bottom gate TFT). Meanwhile, the bottom gate TFT is a thin-film transistor comprised of a gate electrode, a gate insulating film and a polysilicon film (channel layer), sequentially layered on e.g., a glass substrate, beginning from the lower layer side. That is, the bottom gate TFT has a gate electrode formed between the polysilicon film operating as a channel layer and a glass substrate.

Meanwhile, it is said that an important factor determining the electrical field mobility of the polysilicon film is the polysilicon grain size. This grain size depends appreciably on the energy applied to the polysilicon film in excimer laser annealing. Thus, the control and stabilization of the laser power during processing of excimer laser annealing affect the characteristics or the yield of the completed bottom gate TFT significantly.

However, the excimer laser annealing device, used for the processing of the excimer laser annealing, suffers from rather severe fluctuations in the radiated laser power output. Thus, if the excimer laser annealing is carried out using the excimer laser annealing device, the energy afforded to the polysilicon film undergoes significant variations relative to the allowable range of the energy which gives an optimum grain size (the manufacturing margin of the polysilicon film) to render stable production of the polysilicon film difficult.

Thus, even if excimer laser annealing is carried out under the same conditions, the grain size of the polysilicon film is fluctuated significantly, such that, if the laser power becomes excessive, silicon crystals are comminuted to form micro-sized crystals to produce what may be called line defects, whereas, if the laser power becomes too small, the grain size is not sufficient to produce what may be called write defects.

Moreover, in the bottom gate TFT, the gate electrode layer is below the silicon film, so that heat dissipation in case of laser annealing is more significant in a polysilicon film portion lying on the glass substrate (on the source/drain area) than in a polysilicon film portion lying on the glass substrate (on the source/drain area). Consequently, even though the laser power applied from the laser annealing device is the same, the polysilicon film portion on the gate electrode undergoes temperature rise different from that of the polysilicon film portion on the glass substrate (that is on the source/drain area) and, under these effects, the grain size of the polysilicon film on the gate electrode differs from that on the source/drain area. Specifically, with the same laser power, the grain size of the polysilicon film is smaller on the gate electrode than on the glass substrate (on the source/grain area).

Consequently, with the bottom gate TFT, such an energy needs to be applied by the excimer laser which will warrant a grain size optimum for both the polysilicon film on the gate electrode and that on the glass substrate, thus appreciably narrowing the manufacturing tolerance of the polysilicon film.

However, the laser annealing device, used for excimer laser annealing, suffers from larger output fluctuations in the radiated laser power, and hence it is difficult to control the laser power so that both the polysilicon film on the gate electrode and that on the glass substrate will be of the optimum grain size.

Thus, in carrying out the annealing processing with the use of the excimer laser device, the routine practice has been to check for the state of crystals formed on the uppermost surface of the polysilicon film by 100% test or by sampling test, on completion of the poly-crystallizing process of the polysilicon film, in order to verify whether or not the product at this stage is a reject. Moreover, the information as to the energy applied to the polysilicon film is fed back to the excimer laser annealing device to set the laser power.

The apparatus for evaluating the polysilicon film, according to the present embodiment, is used for evaluating the polysilicon film at the stage of completion of the poly-crystallizing process of the polysilicon film, in order to verify whether or not the product at this stage is acceptable, and for feeding the information back to the excimer annealing device, as an aid in setting the laser energy.

Before proceeding to the specified description of the polysilicon film evaluating apparatus, according to the present embodiment, the principle of evaluating the poly-silicon film by the present evaluating apparatus is explained only briefly.

As stated previously, the polysilicon grain size affects the mobility of the ultimate thin-film transistor significantly. For achieving sufficient mobility, a larger polysilicon grain size is desirable.

The grain size of the polysilicon film depends appreciably on the energy afforded by the excimer laser annealing. As may be seen from FIG. 1A, the grain size of the polysilicon film is increased with increase in the energy afforded and, when a preset energy indicated by L in FIG. 1A is reached or exceeded, the grain size is stabilized such that it undergoes only negligible changes. This energy L is referred to as the minimum allowable energy. As the energy is increased further, the grain size change becomes more acute and, if a certain threshold value, indicated by H in FIG. 1A, as a boundary, is exceeded, the polysilicon is turned into micro-sized crystals. The energy H is referred to as the maximum allowable energy.

Thus, in excimer laser annealing, the usual practice is to control the illuminated laser power to within a range from the minimum allowable energy L at which the grain size commences to be stabilized to the maximum allowable energy H at which the grain is about to be turned into micro-sized crystals, to thereby achieve the sufficient grain size. By irradiating an amorphous silicon film with the laser light of the laser power affording this range of the energy, it is possible to warrant a sufficient electrical field mobility of the ultimate thin-film transistor.

An image on the polysilicon film surface in case the excimer laser annealing is carried out at the optimum laser power, an image on the polysilicon film surface in case the excimer laser annealing is carried out at a laser power lower than the optimum laser power and an image on the polysilicon film surface in case the excimer laser annealing is carried out at a laser power larger than the optimum laser power, are to be compared to one another.

Figure 2A:
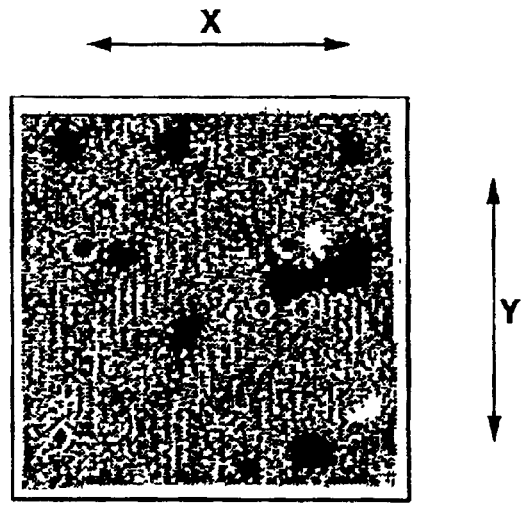
FIG. 2A shows an image of a film surface of a polysilicon film obtained on excimer laser annealing, with the laser power of an optimum value.
Figure 2B:
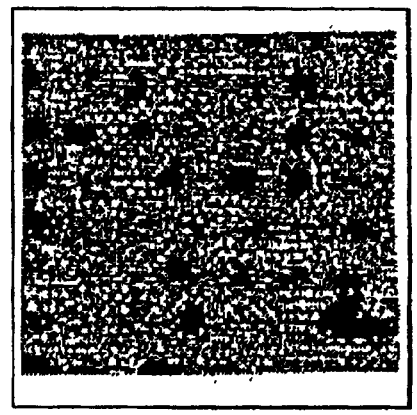
FIG. 2B shows an image of a film surface of a polysilicon film obtained on excimer laser annealing with the laser power lower than the optimum value.
Figure 2C:
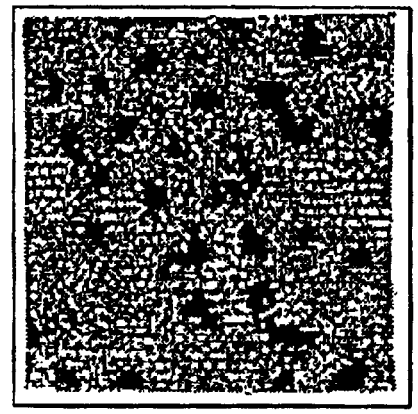
FIG. 2C shows an image of a film surface of a polysilicon film obtained on excimer laser annealing with the laser power larger than the optimum value.

FIGS. 2A to C show the respective images. Specifically, FIG. 2A shows an image on the polysilicon film surface in case the excimer laser annealing is carried out at a laser power lower than the optimum laser power, whilst FIG. 2B shows an image on the polysilicon film surface in case the excimer laser annealing is carried out at the optimum laser power and FIG. 2C shows an image on the polysilicon film surface in case the excimer laser annealing is carried out at a laser power larger than the optimum laser power. Meanwhile, the images shown in FIG. 2 are photographed using a microscope device employing UV light. This microscope device will be explained in detail subsequently.

In FIG. 2, the laser scanning direction of the excimer laser annealing is indicated X. It is noted that the amorphous silicon film is irradiated with a light beam having a rectilinear irradiating surface, with the scanning direction being perpendicular to the longitudinal direction of the irradiating surface of the light beam.

If the image of FIG. 2B, obtained with the optimum laser power in the excimer laser annealing, is compared to the other images, namely the image of FIGS. 2A and 2C, the following characteristics may be noticed.

The image of FIG. 2B on the surface of the polysilicon film, obtained with the optimum laser power in the excimer laser annealing, exhibits linearity as compared to the image of FIG. 2A or 2C on the surface of the polysilicon film, obtained with the non-optimum laser power in the excimer laser annealing. Specifically, the image of FIG. 2B exhibits linearity with respect to the laser scanning direction, indicated X in FIG. 2. That is, the surface of the polysilicon film, obtained with the optimum laser power, features a regular shape characterized by linearity in its spatial structure.

On the other hand, the image of FIG. 2B on the surface of the polysilicon film, obtained with the optimum laser power in the excimer laser annealing, exhibits periodicity as compared to the image of FIG. 2A or 2C on the surface of the polysilicon film, obtained with the non-optimum laser power in the excimer laser annealing. Specifically, the image of FIG. 2B exhibits periodicity with respect to a direction perpendicular to the laser scanning direction, indicated Y in FIG. 2. That is, the surface of the polysilicon film, obtained with the optimum laser power, features a regular shape characterized by periodicity in its spatial structure. In order for this periodic structure to be observed under an optical microscope, it is an optical requirement that the wavelength of the UV rays of the light source be shorter than a value obtained on multiplying this period with the NA of an objective lens of the optical system.

Consequently, with the present embodiment of the polysilicon film evaluating apparatus, the aforementioned feature is exploited to evaluate and test the status of the polysilicon film. That is, with the polysilicon film evaluating apparatus, according to the present embodiment, the surface image of the polysilicon film directly following excimer laser annealing is numerically analyzed to evaluate whether the spatial structure of the surface of the polysilicon film exhibits linearity and/or periodicity, thereby to inspect the status of the polysilicon film of the bottom gate TFT.

Specifically, a numerical value representing the periodicity (an auto-correlation value or AC value) is found from the surface image of the polysilicon film, using auto-correlation, thereby to evaluate the linearity and periodicity of the spatial structure of the polysilicon film surface and to evaluate the status of the polysilicon film.

The processing sequence for evaluation is as follows: First, an image of the surface of the polysilicon film is captured. From the so-captured image, the auto-correlation function is computed. Then, a plane perpendicular to the alignment direction including (0, 0) of the image coordinates is sliced out. A peak value and a side peak value of the auto-correlation function are calculated and the ratio of the peak value to the side peak value is taken to find the AC value, based on which the polysilicon film is evaluated.

Figure 1B:
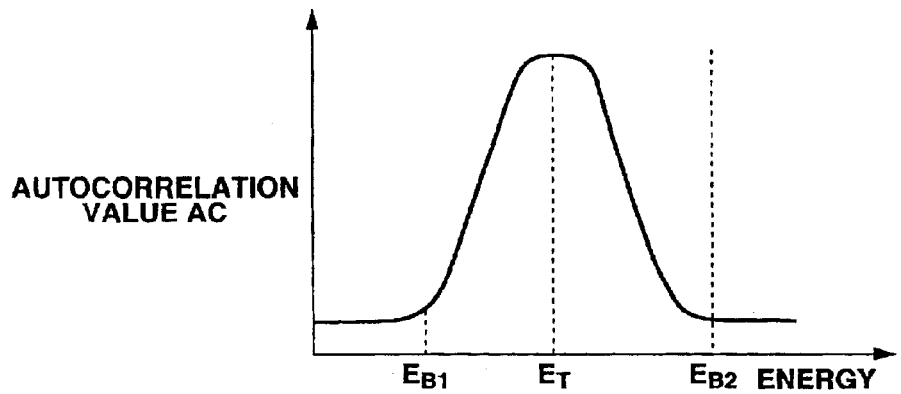
FIG. 1B illustrates characteristics of auto-correlation values (AC values) with respect to the energy afforded to the power source film.

As indicated in FIG. 1B, the AC value increases linearly as from a certain value $E_{B1}$ of the energy, afforded by excimer laser annealing to the polysilicon film, before reaching a maximum value at a certain energy $E_T$. The AC value reaches its peak value at this maximum energy $E_T$ and is decreased proportionally, from that time on, until the decreasing tendency is halted at a certain energy $E_{B2}$ corresponding to a minimum value. Thus, the AC value exhibits peak characteristics with respect to the afforded value of the energy.

Figure 1C:
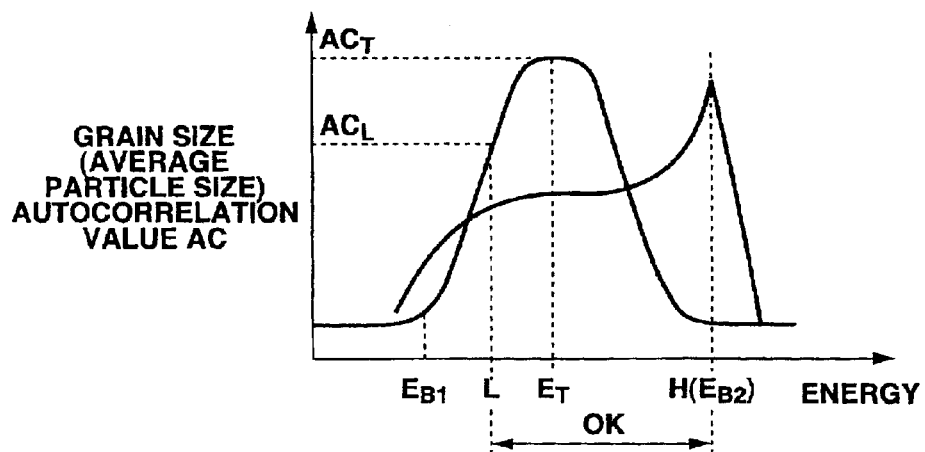
FIG. 1C illustrates characteristics of the auto-correlation values (AC values) and the grain size with respect to the energy afforded to the power source film.

FIG. 1C shows the peak characteristics of the AC value superposed on characteristics of changes in the grain size of the polysilicon film shown in FIG. 1A. As may be seen from FIG. 1C, the maximum value of the graph representing the peak characteristics of the AC value is comprised within the energy range which gives an optimum grain size of the polysilicon film. In addition, the energy $E_{B1}$ corresponding to the start of the proportional rise of the AC value is lower than the minimum allowable energy which, when afforded to the polysilicon film, gives the optimum grain size of the film. Moreover, the energy $E_{B2}$ corresponding to the stop point of the proportional decrease of the AC value at the minimum value corresponds to the maximum allowable energy H which is the energy of a threshold value corresponding to the comminution of the crystal grain size of the polysilicon film to the crystallite size.

Consequently, for evaluating whether or not the grain size of the polysilicon film is optimum, from the AC value having the above-mentioned peak characteristics, it is sufficient if the AC value is verified to be within the range of a thick line in FIG. 1C.

For inspecting whether or not a given polysilicon film is acceptable, based on the evaluation of the AC values having such characteristics, it is checked whether or not the AC value of a substrate being inspected is larger than a threshold value $AC_L$ which may be found on affording the minimum allowable energy L. If the AC value of the substrate being inspected is larger than the threshold value, the substrate being inspected is verified to be acceptable, thus allowing for inspection. If the AC value of the substrate inspected is lower than this threshold value ACL, but if it is found by observing certain characteristics that an energy higher than the energy $E_T$ corresponding to the maximum AC value is being afforded, a decision can be made that the substrate inspected is acceptable.

If, based on the evaluation of the AC values having the above-mentioned characteristics, the laser power emanating from the excimer laser annealing device is to be adjusted to an optimum value, plural substrates are laser-annealed as the laser power of the excimer laser is changed. It is sufficient if the AC values associated with the respective values of the laser power are plotted on a graph, specifically a graph such as one shown in FIG. 1B, and an optimum laser power then is found from the graph.

The structure of a polysilicon film evaluating apparatus for evaluating the status of the polysilicon film for inspection using the aforementioned evaluation principle, is now explained in detail.

In the polysilicon film evaluating apparatus of the present embodiment, a substrate for producing a bottom gate TFT, which is a substrate as formed by excimer-laser annealing an amorphous silicon film to form a polysilicon film thereon, is imaged by a microscope device employing a UV laser with a wavelength of 266 nm, and the status of the polysilicon film formed is evaluated based on the so produced image.

Figure 3:
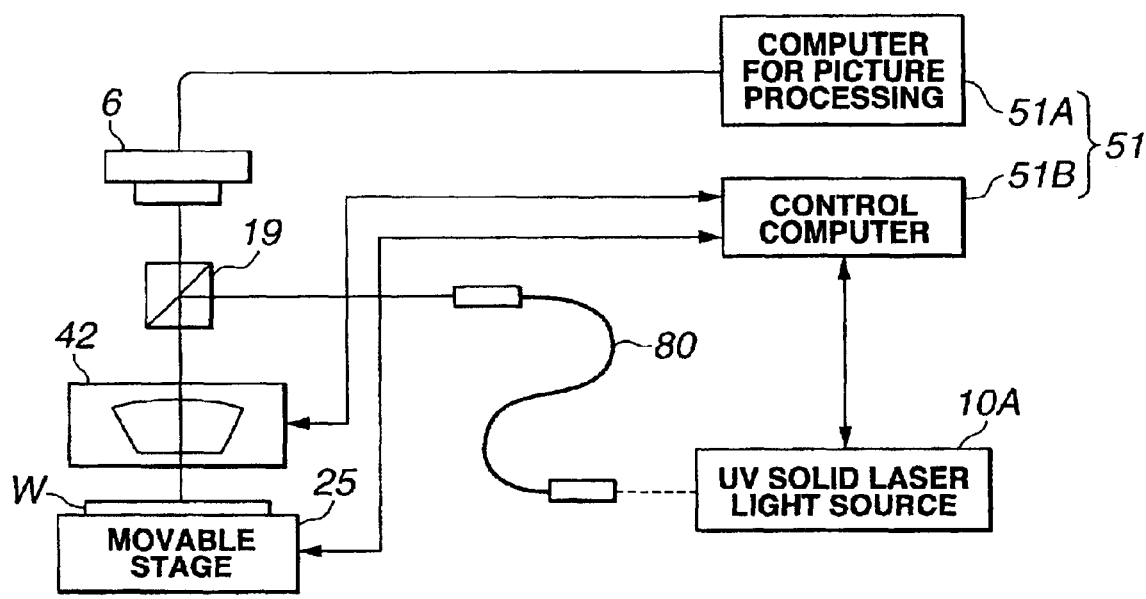
FIG. 3 schematically shows essential portions of a polysilicon film evaluating apparatus shown in FIG. 4.

FIG. 3 schematically shows essential portions of the polysilicon film evaluation apparatus of the present embodiment. As shown, the polysilicon film evaluation apparatus includes a movable stage 25, on which are set a substrate W, a UV solid laser light source 10A, a high-sensitivity low-noise CCD camera 6 for UV light, an optical fiber probe 80, a dichroic mirror 19, a revolver 42, having plural objective lenses, and a controller 51. Meanwhile, the controller 51 is made up of a computer 51A for picture processing and a control computer 51B.

The optical fiber probe 80 is a waveguide path for UV laser light for guiding the UV laser radiated from the UV solid laser light source 10A to a UV illuminating unit 10B. The UV laser, exiting the UV illuminating unit 10B, is sent to the dichroic mirror 19 through a polarizing bean splitter 21 and a quarter wave plate 14.

The dichroic mirror 19 reflects the UV laser light from the UV solid laser light source 10A to illuminate this laser light through one of the objective lenses of the revolver 41 on the substrate W set on the movable stage 25, while transmitting the light reflected from the substrate W therethrough to cause the light to fall on the CCD camera 6 for UV light. That is, the dichroic mirror 19 is a laser light separator for separating the optical path of the optical system for the illuminating light from e.g., the UV solid laser light source 10A and the optical path of the optical system for the reflected light to the CCD camera 6 from each other.

The plural lenses provided on the revolver 42 are optical components for enlarging and detecting the reflected light from the substrate W. These objective lenses are of the NA of, for example, 0.9, and are corrected for aberration at a wavelength of 266 nm. These objective lenses are arranged between the dichroic mirror 19 and the movable stage 25.

The control computer 51B controls the lighting of the laser light of the UV solid laser light source 10A, movement positions of the movable stage 25 or the rotation of the revolver 42 for selecting an objective lens. On the other hand, the picture processing computer 51A captures and analyzes an image of the substrate W, photographed by a CCD image sensor, provided on the CCD camera 6, to evaluate the status of the polysilicon film formed on the substrate W.

In the above-described polysilicon film evaluation apparatus, the UV laser light, radiated from the UV solid laser light source 10A, is illuminated on the substrate W through the optical fiber probe 80, dichroic mirror 19 and through the objective lenses of the revolver 42. The UV laser light, illuminated on the substrate W, is reflected back from the surface of the substrate W, with the reflected light falling on the CCD camera 6 through the objective lenses of the revolver 42 and through the dichroic mirror 19. The CCD camera 6 images the incident reflected light with a CCD image sensor to send the so produced surface image information on the polysilicon film to the picture processing computer 51A. The picture processing computer 51A evaluates the status of the polysilicon film, based on the information of the so captured polysilicon film image information, as will be explained subsequently. Based on the results of the evaluation, the picture processing computer 51A finds the laser power setting values at the time of excimer laser annealing for generating the polysilicon film, or verifies whether or not the polysilicon film formed on the substrate W is acceptable.

Figure 4:
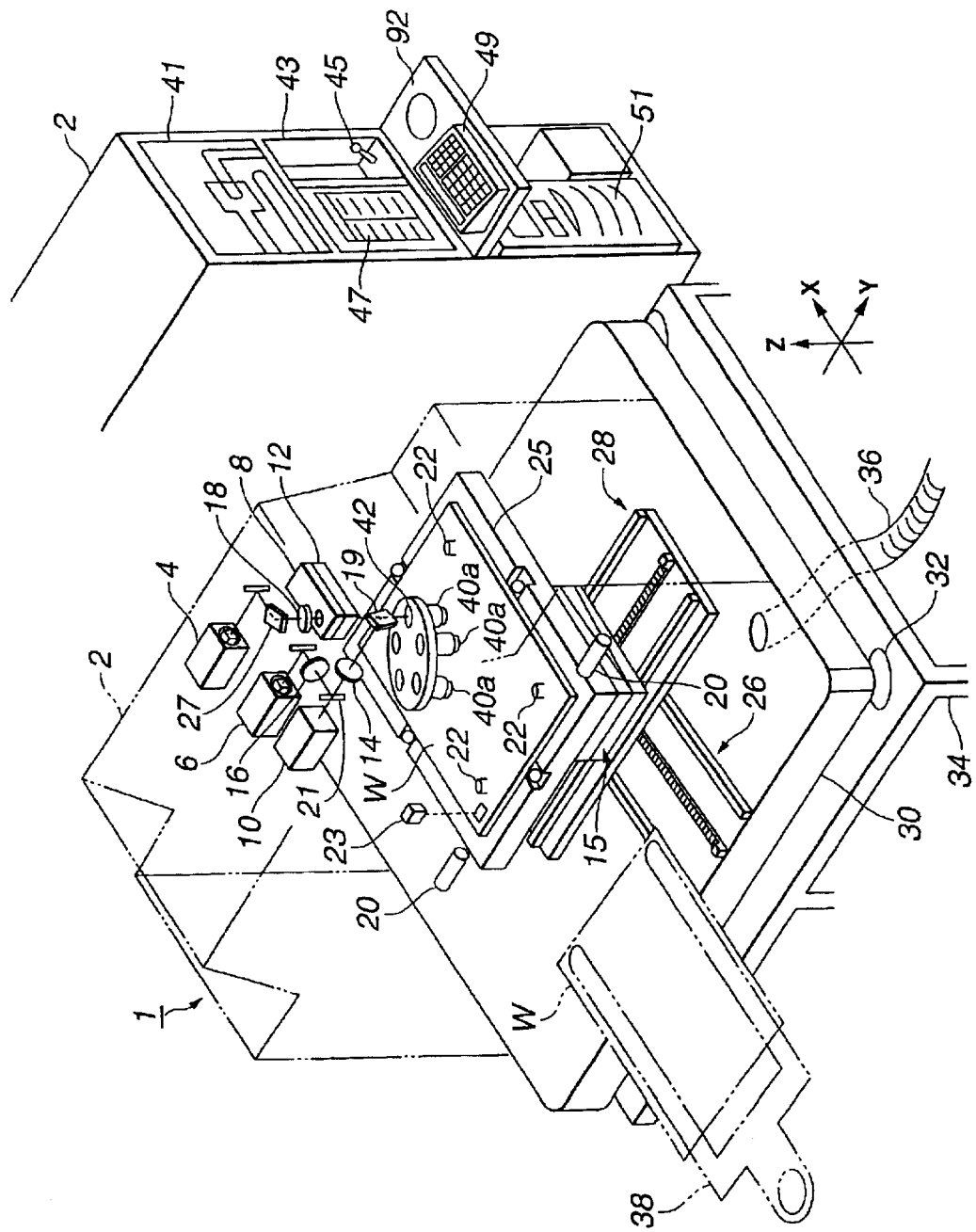
FIG. 4 schematically shows essential portions of an apparatus for evaluating a polysilicon film according to an embodiment of the present invention.
Figure 5:
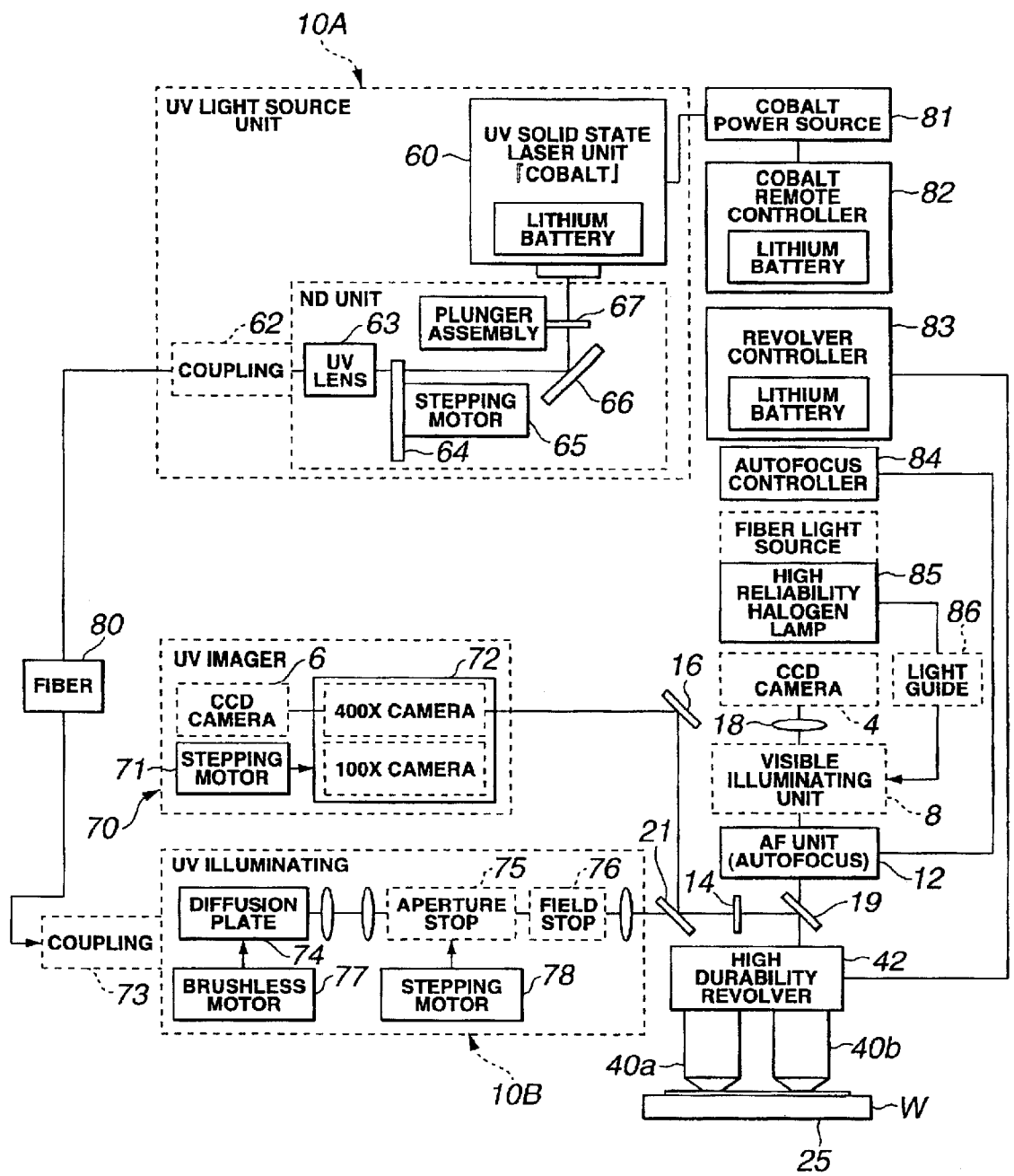
FIG. 5 is a block diagram showing a detailed structure of an optical device of the polysilicon film evaluating apparatus shown in FIG. 4.

Referring to FIGS. 4 and 5, the structure of the polysilicon film evaluation apparatus is explained in further detail.

Referring to FIGS. 4 and 5, the polysilicon film evaluation apparatus 1 of the present embodiment includes an optical system for supplying the visible light, in addition to the optical system for supplying the UV light. The reason is that the objective lens for the UV light exhibits color aberration for the wavelength range of the visible laser light routinely used for auto-focusing, and hence is hardly usable for auto-focusing. Specifically, the apparatus 1 has a visible light illuminating unit 8 and a UV light illuminating unit 10, with the revolver 42 having an objective lens for visible light 40a and an objective lens for UV light 40b. After auto-focusing with the visible light, the revolver 42 is rotated to switch from the objective lens for visible light 40a to the objective lens for UV light 40b and, in this state, the polysilicon film is imaged using the UV light. By the provision of the optical system for the visible light, observation under a microscope also becomes possible.

As the auto-focusing system of the present embodiment, an optical detection system by, for example, a knife edge method, an astigmatic aberration method or an yaw method, or an image processing detection system of detecting the contrast of the image itself to apply the focusing (contrast detection method) may be used. As the image processing detection system, there are also a modulation degree method of applying the focusing using the maximum and minimum contrasts, and a standard deviation method of applying the focusing by exploiting the standard deviation of the contrast. Instead of the optical system, a capacitance detection system of applying the focusing based on the difference in capacitances of mutually approaching objects, may also be used.

As shown in detail in FIG. 5, the optical system for observation with the visible light, adapted for applying the auto-focusing, using the visible light, includes an optical fiber light source 85, comprised of a high reliability halogen lamp, a visible light illuminating unit 8, a light guide 86 for sending the visible light from the optical fiber light source 85 to the visible light illuminating unit 8, an auto-focusing unit 12, an imaging lens 18, a CCD camera for visible light 4 and an auto-focusing controller 84 for controlling the auto-focusing unit 12 based on the image photographed by the CCD camera 4, and executes auto-focusing in known configuration.

The observation optical system for imaging a polysilicon film using the UV light includes a UV solid laser light source (UV light source unit) 10A, a UV light illuminating unit (UV illuminating unit) 10B and a UV light imaging unit (UV imaging unit) 70.

The UV ray solid laser light source 10A is made up of a UV solid state laser unit 60 and an ND unit 61. The UV solid state laser unit 60 is a UV laser light source with a wavelength of 266 nm and uses e.g., Nd:YAG quadrupled wave full solid state laser. As this UV laser light source, such a light source with a wavelength of the order of 157 nm, recently developed, may be used as a light source.

The ND unit 61 includes a UV lens 63, a UV mirror 66 for reflecting the UV light from the UV solid state laser unit 60 towards the UV lens, a UV shutter 67 provided on an optical path between the UV solid state laser unit 60 and the UV mirror 66, and a variable ND filter 64 provided on the optical path between the UV lens 63 and the UV mirror 66 for adjusting the brightness at the time of observation with the UV light. In this case, the UV shutter 67 operates in known manner by a plunger assembly 68, while the variable ND filter 64 operates in known manner by a stepping motor 65 for adjusting the aperture ratio.

The UV light illuminating unit 10B includes a diffusion plate 74 for receiving the UV light from the UV solid laser light source 10A, an aperture stop 75 and a field stop 76. The diffusion plate 74 operates in known manner by a DC brushless motor 77. The aperture stop 75 also operates in known manner by a stepping motor 78.

Meanwhile, the UV light from the UV ray solid laser light source 10A is transmitted to the UV illuminating unit 10B by an optical fiber interconnecting a coupling 62 of the ND unit 61 of the UV solid laser light source 10A and a coupling 73 of the UV illuminating unit 10B.

The UV light imaging unit (UV imaging unit) 70 includes a CCD camera for UV light 6 and a multiplication lens system 72. The multiplication lens system 72 includes e.g., a lens for multiplication by 400 and a lens for multiplication by 100. A stepping motor 71 is used to select a lens. The CCD camera 6 is a camera highly sensitized with respect to the UV light, and includes a CCD image sensor, as an internal imaging device for imaging the surface of the substrate W. The CCD camera has its main body unit cooled to suppress thermal noise produced in the CCD image sensor, read-out noise or the noise emanating from the circuitry.

In FIGS. 4 and 5, 16 is an imaging lens for UV light, 21 is a beam splitter, 14 is a wavelength plate provided on an optical path between the beam splitter 21 and the dichroic mirror 19, 22 is a vertically movable pin mounted on the stage 25 for hoisting the substrate W on the stage 25, and 23 is a reference detection sensor for detecting the positioning state of the substrate on the stage 25. 83 is a revolver controller for rotating the revolver 42 to switch between the objective lens for visible light 40a and the objective lens for UV light 40b. The substrate W is a large-sized rectangular liquid crystal substrate of, for example, 600 mm by 720 mm, and is transported one-by-one to a stand-by position, not shown, where it is kept in the stand-by state before being loaded one at a time onto the stage 25 by a robot arm 38.

The movable stage 25 also has the function of supporting the substrate W, now carrying the polysilicon film formed thereon for inspection, and of shifting the substrate W to a preset inspection position. Specifically, the movable stage 25 is movably carried by an X-stage 26 adapted for shifting the stage 25 along the X-axis direction, a Y-stage 28 adapted for shifting the stage 25 along the Y-axis direction, and a Z-stage 15 adapted for shifting the stage 25 along the Z-axis direction. That is, the movable stage 25 causes the substrate W to be moved in mutually perpendicular directions, by the X-stage 26 and the Y-stage 28, for setting the substrate W at a preset inspection position. The movable stage 25 also has its height adjusted by the Z-stage 15 to contribute to the focusing operation. The X, Y and Z stages 15, 26, 28 are stationarily set on a table 30 mounted on a support 34 through e.g., a plural number of dampers (vibration dampers) 32 each comprised e.g., of a pneumatic spring.

Figure 6:
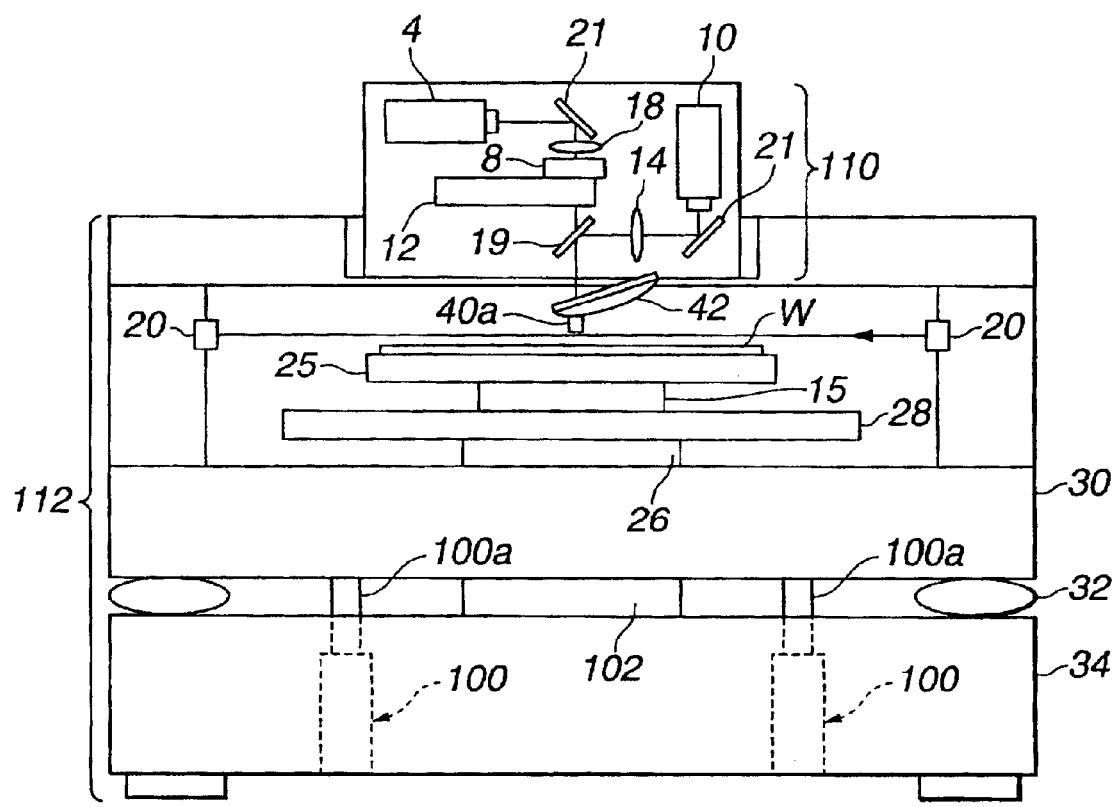
FIG. 6 schematically shows the entire polysilicon film evaluating apparatus shown in FIG. 4.
Figure 9:
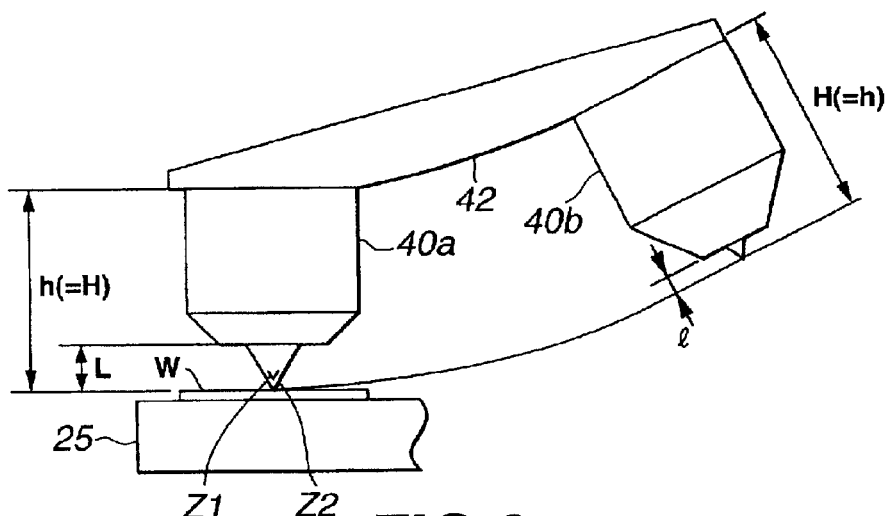
FIG. 9 is a schematic view showing a conventional form corresponding to FIG. 10.

The aforementioned optical systems for observation with the visible light and for observation with the UV light are formed as a sole integral unit to facilitate maintenance and is removably mounted on the main body unit 2 of the apparatus. FIG. 6 shows the loading state. As shown in FIG. 6, the apparatus 1 is comprised of an optical section 110, having the optical systems for observation with the visible light and for observation with the UV light, and a mechanical section 112, as the main body unit 2, including the stage 25 and its driving systems 15, 26, 28. That is, the apparatus 1 carries the optical system and an XYZ movement mechanism on its upper and lower portions, respectively. With such construction, an optical system can be assembled, e.g., set for alignment, on an optional site. Moreover, the optical system 110 can be built into the main body unit 2, that is into the mechanical section 112, provided only that the geometry of the optical section 110 and mechanical section 112 is accurate. Moreover, the optical system allows easy maintenance since the optical section 110 need only be dismounted from the mechanical section 112.

Referring to FIG. 4, an air exhaust duct 36 is connected to the main body unit 2 to warrant forced air exhaust from the main body unit 2. A control tower is provided on the main body unit 2 adjacent to an inspection area. This control tower is provided with an operating desk 92, an image display monitor 41, an operating panel (touch display) 47, a joystick 45 for operating the X, Y and Z stages 15, 26, 28, and a controller 51. On the operating desk, there is mounted an operating keyboard 49.

The joystick 45 is provided in a recess 43 in the main body unit 2 so as not to protrude to the outside. That is, as shown enlarged in FIG. 7, the joystick 45 is laid out in the recess 43 formed in the main body unit 2 e.g., by bending a metal sheet so as not to protrude from the surface of the main body unit. For comparison, the layout of the conventional joystick is shown in FIGS. 8A and 8B. As shown therein, conventional joysticks P, Q are laid out so they stick out over or from the operating desk. The result is the risk of malfunctions due to inadvertent contact or of the space of the operating desk being taken up by the joysticks P, Q. Conversely, with the present embodiment, laid out as shown in FIG. 7, such malfunctions resulting from the contact with the joystick 45 may be prevented from occurrence. Moreover, space saving may be achieved, while the labor of dismounting the joystick 45 for re-packaging for transport may be dispensed with to diminish the number of transport steps. In addition, since the bottom surface of the recess 43 is inclined, the joystick 45 may be improved in tractability. Meanwhile, the layout exploiting the recess 43 may be applied not only to the joystick 45 for operating the XYZ stage but also to a jog dial, track ball, touch pad or to a keyboard.

Moreover, in the present embodiment, there is provided first collision preventative means for preventing collision of the substrate W against the objective lens, in particular the objective lens for UV light 40b having only a small working distance, and resultant damage thereof, in case the dampers 32 used for interconnecting the substrate W and the support 34 is wobbled by the oscillations applied from outside. This first collision preventative means optically senses the movement along the X-direction of the substrate W for regulating such movement. That is, the first collision preventative means includes a substrate float sensor 20 for providing a laser light beam between two sensor sections facing each other on both sides of the upper limit position of the movement path along the Z-direction of the movable stage 25. When the stage 25 is caught by the laser light of the sensors 20, that is when the laser light has detected that the stage 25 has reached the upper limit position along the Z-direction, the first collision preventative means forcibly halts the driving of the Z-stage, or issues an alarm.

In connection with the collision of the substrate W against the objective lens, in particular the objective lens for UV light 40b having only a small working distance, the upper limit position of the Z-stage 15 is a function of the XY coordinates in the XY stages 26, 28 in the present embodiment. That is, the upper limit position of the Z-stage 15 changes depending on its position on the XY plane, that is on the flatness of the XY plane. Specifically, the setting value of the limit stop position along the Z-direction in the software technique is adapted to be switched automatically depending on the coordinate positions of the XY stages 26, 28. Thus, the above-mentioned setting values are mapped depending on the state of pre-measured inundations of the upper surface of the movable stage 25. This function enables the setting margin of the limit position to be maintained since the reproducibility of the movement performance of the movable stage 25 is not larger than 0.01 mm even in case an inexpensive mechanical guide is used. Conventionally, a limit switch is provided by a hardware or software technique to halt the approaching movement at a position directly ahead of the impending collision in order to prevent the substrate and the objective lens from contacting each other. However, if, with the increasing size of the substrate W being observed, the plano-parallelism of the entire XY area of the setting surface of the stage 25, on which to set the substrate W, is worsened, the possible setting range becomes extremely small with microscopical observation employing a high multiplication objective lens 40b having a large NA and a small working distance WD. For example, scarcely any allowance can be provided with WD=0.2 mm and with plano-parallelism=0.1 mm. Thus, in such case, an expensive XY stage with stringent plano-parallelism is required. This problem can be overcome by setting the upper limit halt position of the Z-stage 15 as a function of the XY coordinates in the XY stages 26, 28, as in the present embodiment.

Figure 10A:
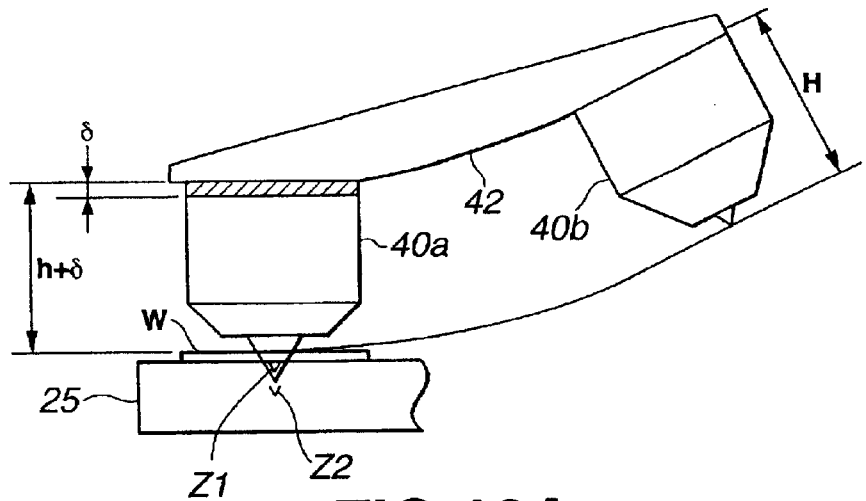
FIG. 10 schematically shows means for preventing interference between an objective lens and a substrate by intentionally setting WD of an objective lens for UV rays to a larger value.
Figure 10B:
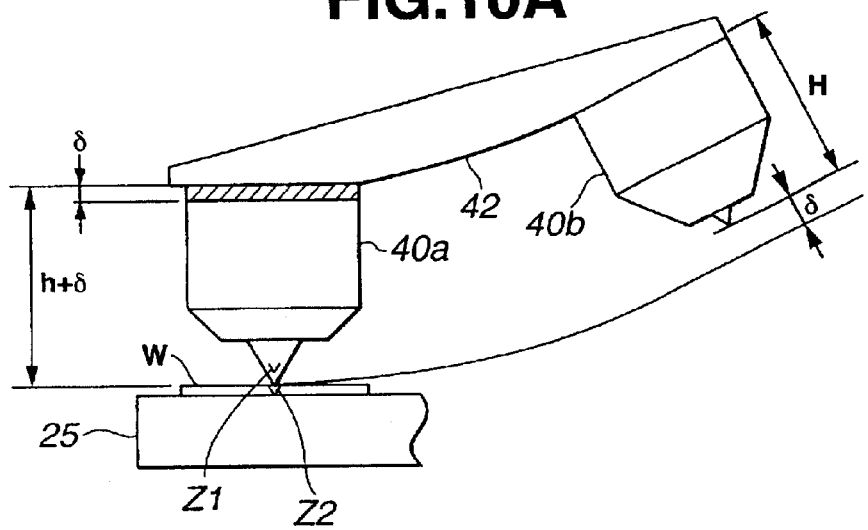
Figure 11:
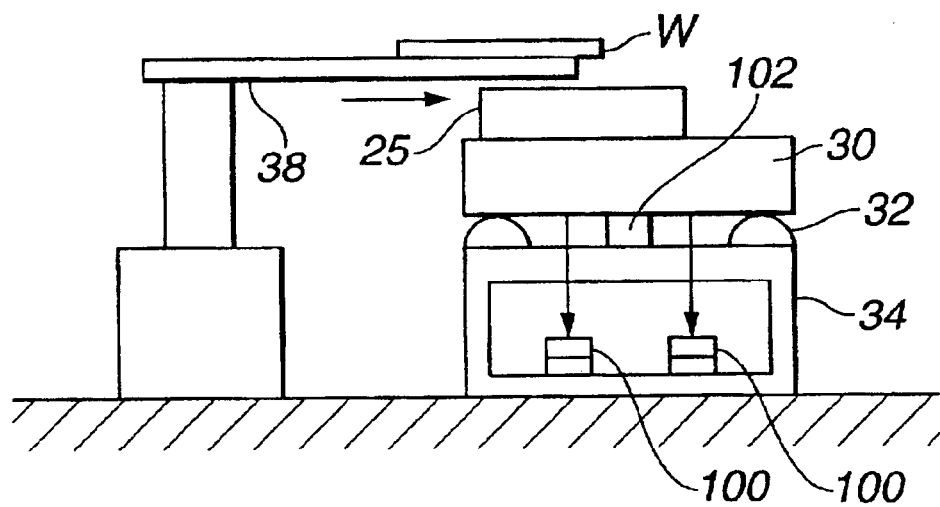
FIG. 11 is a schematic view showing collision preventative means used for preventing collision of a substrate loaded on a stage against the stage.

Moreover, in connection with the interference between the substrate W and the objective lens, in particular the objective lens for UV light 40b having only a small working distance, the following measures are taken in the present embodiment: If, in case plural objective lenses 40a, 40b having different values of the WD are provided on the revolver 42, as in the present embodiment, the revolver 42 is rotated to switch between the objective lenses, as the objective lens for visible light 40a with a larger WD, such as with L=2 mm or more and with the focal length h, is focused at a near point Z2, Z1 being a distant point in the drawing, there is a risk of the objective lens for UV light 40b with the small WD, for example, with L approximately equal to 0.1 mm and with the focal length H (=h), colliding against the substrate W. Thus, in the present embodiment, the WD of the objective lens for UV light 40b is intentionally set to be larger by δ, as shown in FIG. 10. In FIGS. 10A and 10B, the objective lens for visible light 40a is focused at the near point Z2 and at the distant point Z1, respectively. If the objective lens for visible light 40a with the larger value of WD approaches the substrate W, it is possible to prevent the objective lens for UV light 40b from colliding against the substrate W by virtue of the allowance corresponding to the distance δ.

Also, in the present embodiment, in which the table 30 and the support 34 are interconnected by the dampers 32, there is a risk that, when the dampers 32 are wobbled by external oscillations, the stage 25 is oscillated to cause collision of the substrate W transported by the robot arm 38 against the stage 25. In order to prevent such collision from occurring, the present embodiment provides second collision preventative means. As shown clearly in FIG. 6, this second collision preventative means includes e.g., a pneumatic cylinder 100 secured to the support 34. This pneumatic cylinder 100 includes an extensible rod 100a connected to the table 30. Between the table 30 and the support 34 is provided a stop 102.

Figure 12:
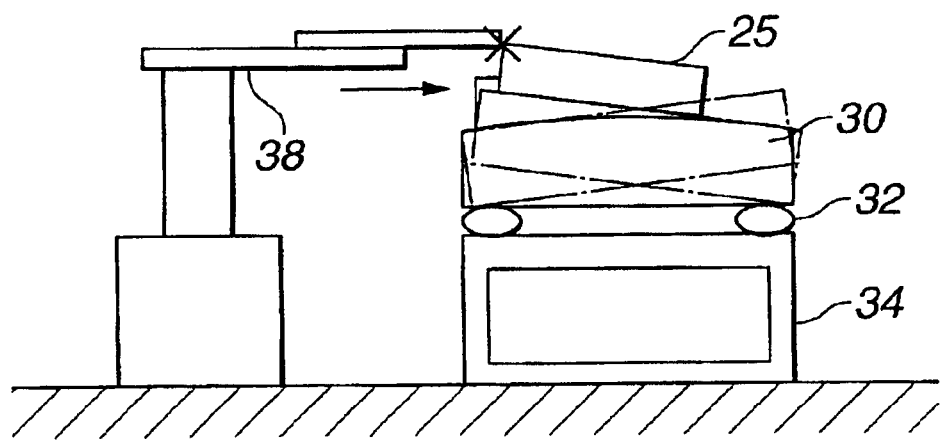
FIG. 12 is a schematic view showing a conventional form corresponding to FIG. 11.

FIG. 12 shows the state of use of the second collision preventative means. First, when the substrate W is loaded on (or unloaded from) the stage 25 by the robot arm 38, the inside of the dampers 32, made up of pneumatic springs, is evacuated and the table 30 on the upper side of the dampers 32 is pulled downwards by the pneumatic cylinder 100. This causes the lower surface of the table 30 to be abutted against the stop 102 to secure the table 30 in position. If this immobilized position is detected by detection means, not shown, the robot arm 38 loads the substrate W on the stage 25 or unloads the substrate W from the stage 25. Once the substrate W is set on the stage 25, the dampers 32 are again supplied with air to set the damper mechanism in operation. That is, the stage 25 can be switched between a first state in which it is mounted on the support 34 through the interposition of the dampers (oscillation damping means) 32 adapted for preventing oscillations of the stage 25 to render the dampers 32 capable of preventing the oscillations, and a second state in which the stage 25 is secured to the support 34 to render the dampers 32 incapable of preventing the oscillations. Lacking the second collision preventative means, there is a risk that the dampers 32 are oscillated at the time of delivery or receipt of the substrate W to or from the stage 25 to cause collision of the substrate W on the arm 38 against the stage 25, as shown in FIG. 12.

Thus, with the second collision preventative means, the oscillations of the dampers 32 can be eliminated to warrant safe delivery or receipt of the substrate W. If only the inside of the usual pneumatic spring is evacuated, the time until abutment of the table 30 against the stop 102 is protracted. If the table 30 is positively pulled with the aid of the cylinder 100, as in the present embodiment, the tact time can be shortened to ultimately improve the operating efficiency.

Moreover, in the present embodiment, the optical system for observation with the visible light and that for observation with the UV light are arranged on the same axis, as shown in FIGS. 4 to 6 and 13, in such a manner that, using the auto-focusing functions provided on the optical system for observation with the visible light, the focusing at the time of observation with the UV light can be achieved extremely readily. That is, in the present embodiment, the objective lens for visible light 40a can be changed over to the objective lens for UV light 40b, on the same focal point, or vice versa, using the revolver 42, with the result that auto-focusing may be first achieved with the optical system for observation with the visible light and subsequently the optical system for observation with the UV light can be focused readily subject only to lens switching on the revolver 42. Conversely, if the conventional reflection active auto-focusing, employing the visible or IR laser light, is applied to the optical system for observation with the UV light, optimum performance cannot be obtained due to color aberration proper to the objective lens for UV light 40b. Although a lens with corrected color aberration in a range from the UV to visible light is usable, such lens is extremely costly, while there is raised a problem of deterioration due to UV light radiation under the effect of the adhesive used in the manufacture process. If an achromatic lens, substantially free from the problem of deterioration, is used, the optical system for the visible portion and that for the UV light, although costly, can be constructed independently of each other. An auto-focusing mechanism may also be provided independently on each of the optical systems. Since there is provided only one objective lens for the UV light, the revolver mechanism has only the objective lens for the visible light, so the objective lens for the UV range can be driven with a piezo actuator. The system of driving the objective lens by the piezo actuator has an advantage over the case of performing fine adjustment for Z on a lower base, specifically, an advantage that the inertial moment is decreased to shorten the auto-focusing tact time.

Figure 13:
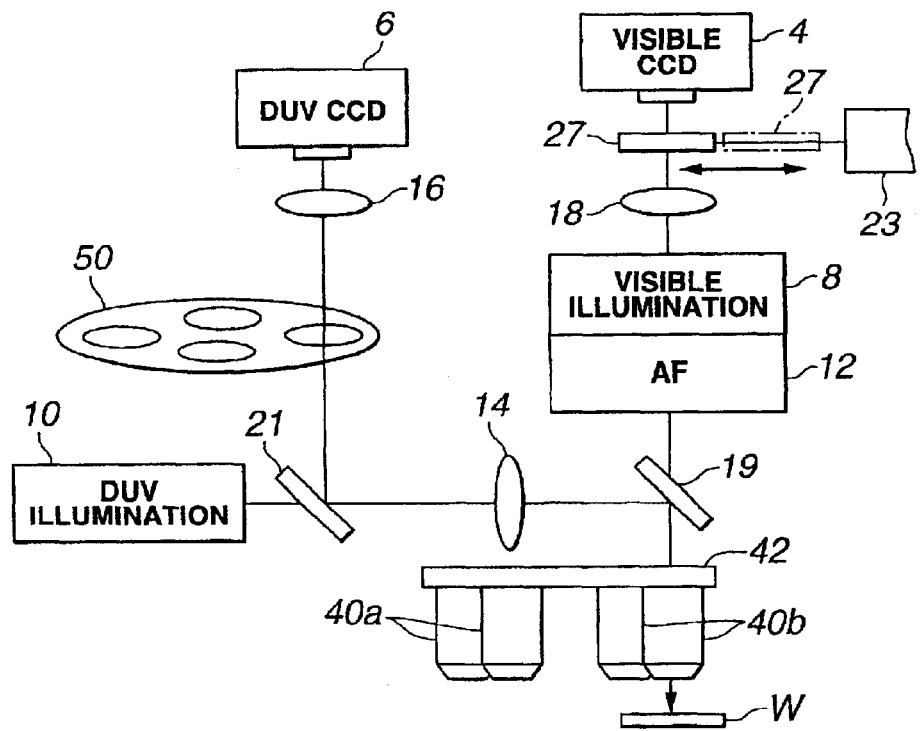
FIG. 13 schematically shows an optical device of the polysilicon film evaluating apparatus shown in FIG. 4.

Moreover, in the present embodiment, a filter 27 for eliminating the auto-focusing (AF) light wavelength is telescopically fitted between the CCD for visible light 4 and the imaging lens 18, as shown in FIG. 13. In this case, the telescopic movement of the filter 27 is performed by a filter shifting mechanism 23. Specifically, the filter 27 is used, that is placed on the optical path, when focusing is applied, while it is removed from the optical path when the image is viewed. If the filter 27 is removed after focusing, and the image is viewed stationarily, obtained is a full-color image. If reflection active type auto-focusing is applied with the use of the light of the visible wavelength range such as 660 nm red, as is the case with the conventional systems, it becomes necessary to insert a filter for cutting off the wavelength of the focusing light on the optical axis of the light for illumination for observation in order to suppress the effect of the illuminated light on the focusing accuracy. Since the red light component of the illuminated light is cut in this case, the image being observed is of a bluish color, making full-color image observation impossible.

Meanwhile, in the present embodiment, a liquid crystal variable filter without actuating components may also be used as the filter 27. A color filter 50 may also be inserted on an optical path between the CCD for UV light 6 and the beam splitter 21, as shown in FIG. 13.

Figure 14:
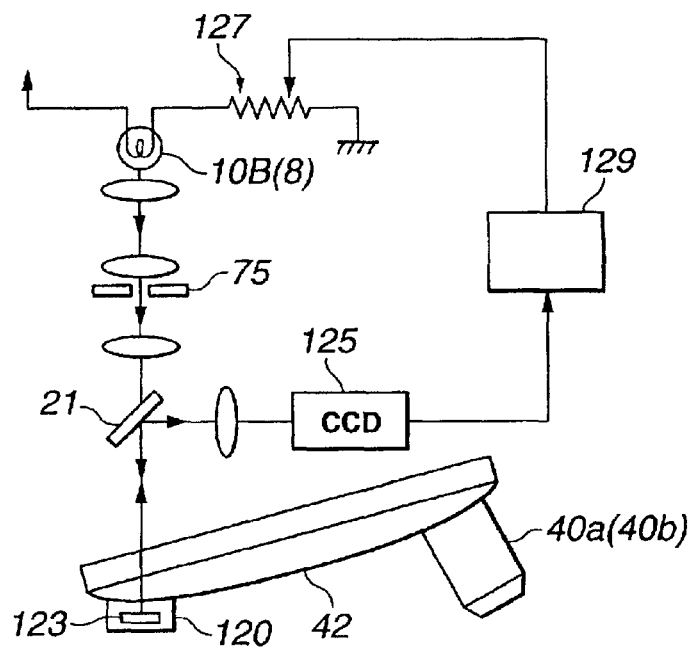
FIG. 14 is a schematic view showing a mechanism for controlling the illuminated light volume.

In the present embodiment, five objective lenses may be mounted on the revolver 42. However, the objective lenses are set only in four of the five lens mounting sections of the revolver 42. Specifically, two objective lenses for visible light 40a and two objective lenses for UV light 40b are set on the revolver 42. Additionally, the present embodiment includes a light volume control mechanism for monitoring and adjusting the volume of light illuminated on the substrate W. This light volume control mechanism includes a reflecting mirror 123 for reflecting the illuminated light incident on the objective lens, a CCD 125 for receiving the light, reflected back form the reflecting mirror 123, under the light reflecting action of the beam splitter 21, and a light illumination volume controller 129 for adjusting the volume of the illuminated light to a preset value by varying the resistance value of an electrical component 127, such as a variable resistor, of the illuminating optical system, based on the image as photographed by the CCD 125, as shown in FIG. 14. In this case, the reflecting mirror 123 is set on the remaining one void lens mounting section 121 of the revolver 42 not carrying the objective lens.

Figure 15A:
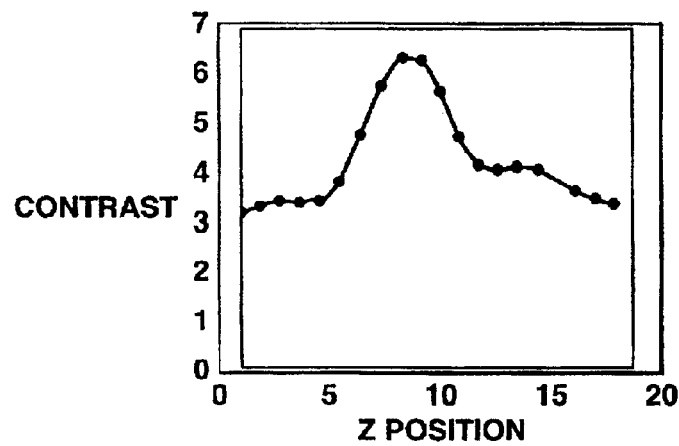
FIGS. 15A to 15C are graphs showing the contrast of data obtained on shifting the WD vertically of the stage in the same direction as the initial inspection WD at constant-pitch steps.

It should be noted that, since the present embodiment uses an optical system with an extremely shallow depth of focus (objective lens for UV light 40b), plural number of images having different focus values in the vicinity of the best focus need to be captured and evaluated in order to acquire an image of the best focus by the CCD camera for UV light 6. To this end, the apparatus 1 has the learning function of finding an image of the best focus from as small a number of images as possible to thereby reduce the processing time. If plural articles for inspection (substrates W) of the same lot are batch-processed as being of the same lot in the directly previous step, such learning function is effective because different patterns of the same lot tend to manifest the same tendency. The specified learning sequence of the learning function is now explained. First, the value of standard deviation is calculated from the distribution of the Gray values of the same site and the same area. It is empirically known that, if plural images of different focus values are captured, the image with the maximum standard deviation is of the maximum contrast and of the maximum auto-correlation coefficient value (AC value). The polysilicon film evaluation apparatus 1 of the present embodiment has a structure capable of setting the WD to a high accuracy. The WD is varied, as from the inspection start WD, at a constant pitch, in the same direction vertically of the stage 25, thereby to acquire data. FIG. 15A shows a graph of standard deviation of the acquired data. From these data, an image with a peak position is used as being the best focus image for the subsequent analysis.

In the graph of FIG. 15A, the abscissa and the ordinate denote the defocus positions along the Z-direction and the standard deviation, that is contrast, respectively. The values of the standard deviation on either sides of the targeted maximum value of the standard deviation are measured as a preliminary inspection for finding a peak value. The extent of this preliminary inspection is preferably as small as possible in consideration of the measurement efficiency. The shortest cut algorithm of finding this peak value P is what has been termed the learning function.

Figure 15B:
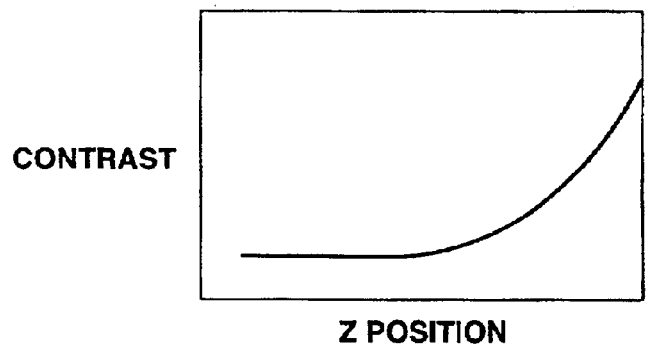
Figure 15C:
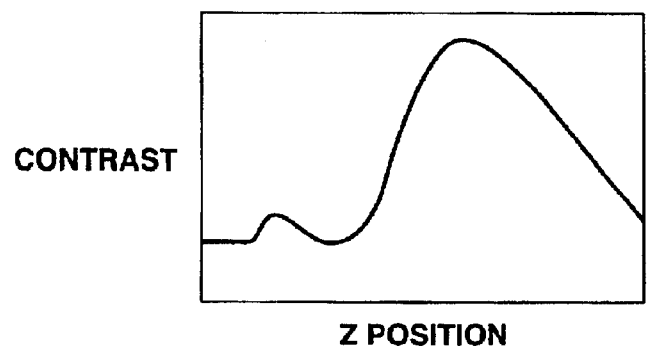

The conditions of deciding the measurement start position, WD scanning width, the total number of times of scanning and the peak represent four elements for decision. First, the peak position is acquired by a manual operation. At this time, the initial peak is extracted, without regard to the number of times of scanning. From the second scanning, measurement is made by performing N times of scanning about the peak to calculate the standard deviation. As a result, the following four states are obtained:

a. a state with a peak;
   b. a state without a peak, with an ascending curve (see FIG. 15B);
   c. a state without a peak, with a descending curve; and
   d. a state with more than one peak (see FIG. 15C).

If, with the number of times of the focusing scanning N, the peak is obtained in a previous case, it is calculated at which number of times of scanning the peak value has appeared. The focusing scanning is then carried out as the start position is changed so that the peak will be at the mid point of the total scanning width. Simultaneously, the scanning is carried out as the number of times of scanning is decreased drastically.

If the curve is rightwardly ascending, without a peak (see FIG. 15B), the start position is shifted to the right by one-half width to then proceed to focus scanning. If a curve as measured is descending, without a peak, the start position is shifted to the left by one-half width to then proceed to focus scanning. If plural peaks appear (see FIG. 15C), the peak with the larger standard deviation is searched. A the case may be, the second or third peak is also searched on the condition that, if a peak has been detected, a change in the standard deviation from a neighboring point exceeds a prescribed value. Since the above-described algorithm does not necessarily guarantee success, limitations are imposed on the number of times measurement is repeated. The overall efficiency can be improved if measurement is continued in this algorithm as the sequence is changed each time.

Although the focusing is done automatically on the apparatus 1, there may be occasions where manual focusing is preferred or where it is desirable to check whether or not the focusing is proceeding accurately on the apparatus 1. To this end, the strength distribution is plotted on a monitor 41. Specifically, the luminosity on the scanning line indicated by a broken line is plotted on a graph and superimposed on a surface image on the polysilicon film. From these graphs, the point of the most acute angle of an edge S (see FIG. 16B) may be determined to effect focusing with high reproducibility.

The luminosity, once differentiated, may further be superimposed, as shown by way of an example in FIG. 17 where F, F' denote luminosity and rate of change thereof, respectively. The maximum range H may be regarded as being focusing range.

What is claimed is:

1. An apparatus for evaluating a polysilicon film formed by annealing an amorphous silicon film, comprising:

a stage configured to receive a substrate thereon, said substrate carrying a polysilicon film formed thereon;

a first optical system configured to observe visible light, said first optical system illuminating the visible light on said substrate on said stage for photographing a surface image of said polysilicon film on said substrate to effect auto-focusing;

a second optical system configured to observe UV light, said second optical system illuminating the UV light on said substrate on said stage for acquiring a surface image of said polysilicon film on said substrate, auto-focused using said second optical system for observation with the visible light; and evaluation means for evaluating the linearity and periodicity of a spatial structure of a film surface of said polysilicon film from the surface image of said polysilicon film acquired by said second optical system to evaluate a state of said polysilicon film based on evaluation of said linearity and periodicity.

2. The polysilicon film evaluation apparatus according to claim 1 wherein a wavelength of said UV light is shorter than an evaluation period of said polysilicon film multiplied by a numerical aperture (NA) of an objective lens for observation in said second optical system.

3. The polysilicon film evaluation apparatus according to claim 1 or 2 wherein said stage may be switched between a first state in which said stage is mounted on a support via oscillation preventative means for preventing oscillations of said stage so that an oscillation preventative operation by said oscillation preventative means occurs, and a second state in which said stage is secured to said support so that said oscillation preventative operation ceases.

4. The polysilicon film evaluation apparatus according to claim 1 wherein said first optical system and said second optical system are an integral unit.

5. The polysilicon film evaluation apparatus according to claim 4 wherein said unit is detachably loaded at an upper portion of a main body unit of the apparatus where said stage is mounted.

6. The polysilicon film evaluation apparatus according to claim 1 further comprising:

a rotatable revolver integrally carrying thereon an objective lens for visible light of said first optical system and an objective lens for UV light of said second optical system wherein a state of use of said objective lens for visible light and said objective lens for UV light is changed over on rotational operation of said revolver.

7. The polysilicon film evaluation apparatus according to claim 6 further comprising:

light volume control means for controlling a volume of illuminated light of at least one of said first and second optical systems;

said light volume control means including a reflection mirror for reflecting the illuminated light for monitoring the volume of illuminated light; and said reflecting mirror being provided in a vacant region of said revolver.

8. The polysilicon film evaluation apparatus according to claim 1 wherein said stage is movable along three axes perpendicular to one another, that is along X-, Y- and Z-axes;

an upper limit position along the Z-axis direction of said stage being set as a function of XY coordinates in meeting with smoothness of an XY plane of said stage.

9. The polysilicon film evaluation apparatus according to according to claim 1 wherein said evaluation means captures a plurality of surface images of said polysilicon film with different focus values, by said second optical system, to acquire an image with an optimal focus; and wherein said evaluation means has a learning function to acquire the image of the optimal focus with a decreasing number of images captured with an increasing number of times of evaluation operations.

* * * * *